| (12) | United States Patent | (10) Patent No.: US 10,052,130 B2 |
|---|---|---|
| | Richey | (45) Date of Patent: *Aug. 21, 2018 |

(54) VAGINAL SURGICAL APPARATUS

(71) Applicant: Freshwater Bay Industries, LLC, Anchorage, AK (US)

(72) Inventor: Mark Edmund Richey, Anchorage, AK (US)

(73) Assignee: Freshwater Bay Industries, LLC, Anchorage, AK (US)

( * ) Notice: Subject to any disclaimer, the term of this patent is extended or adjusted under 35 U.S.C. 154(b) by 145 days.

This patent is subject to a terminal disclaimer.

(21) Appl. No.: 15/480,227

(22) Filed: Apr. 5, 2017

(65) Prior Publication Data

US 2017/0202578 A1  Jul. 20, 2017

Related U.S. Application Data

(63) Continuation of application No. 15/208,867, filed on Jul. 13, 2016, now Pat. No. 9,655,646, which is a
(Continued)

(51) Int. Cl.
    *A61B 17/42* (2006.01)
    *A61B 90/00* (2016.01)
    (Continued)

(52) U.S. Cl.
    CPC ...... *A61B 17/4241* (2013.01); *A61B 1/00066* (2013.01); *A61B 1/00179* (2013.01);
    (Continued)

(58) Field of Classification Search
    CPC . A61B 17/4241; A61B 17/0483; A61B 1/303; A61B 1/0684; A61B 1/00066;
    (Continued)

(56) References Cited

U.S. PATENT DOCUMENTS

| 1,940,122 A | 8/1931 | Gardner |
|---|---|---|
| 3,587,588 A | 9/1971 | Muir |
| (Continued) | | |

FOREIGN PATENT DOCUMENTS

| RU | 81947 | 10/2003 |
|---|---|---|
| RU | 44050 | 2/2005 |
| SU | 133553 | 10/1960 |

OTHER PUBLICATIONS

Nygaard et al. "Abdominal Sacrosolpolexy: A Comprehensive Review", Obstet Gyne, Oct. 2004, 104(4)805-823.
(Continued)

*Primary Examiner* — Christine H Matthews
*Assistant Examiner* — Joshua D Lannu
(74) *Attorney, Agent, or Firm* — Ruttler Mills, PLLC; James J. Ruttler

(57) ABSTRACT

This invention relates generally to a medical device, and more specifically, to a vaginal surgical apparatus. In one embodiment, an apparatus includes, but is not limited to, an elongated handle portion; a vaginal manipulator probe that is at least partly insertable into a vagina, the vaginal manipulator probe extending from the elongated handle portion and including an arcuate end portion, the arcuate end portion including an aperture for accommodating a cervix; and a disk that is movable along at least a portion of a length of the vaginal manipulator probe, the disk including a locking mechanism to releasably secure the disk in position to limit vaginal insertion depth of the vaginal manipulator probe.

20 Claims, 6 Drawing Sheets

Related U.S. Application Data continuation of application No. 15/179,215, filed on Jun. 10, 2016, and a continuation-in-part of application No. 13/852,784, filed on May 31, 2013, and a continuation-in-part of application No. 14/971,512, filed on Dec. 16, 2015.

(60) Provisional application No. 62/174,127, filed on Jun. 11, 2015, provisional application No. 62/193,721, filed on Jul. 17, 2015, provisional application No. 62/252,810, filed on Nov. 9, 2015, provisional application No. 62/257,090, filed on Nov. 18, 2015, provisional application No. 62/295,038, filed on Dec. 9, 2015, provisional application No. 62/312,069, filed on Mar. 23, 2016.

(51) Int. Cl.
  *A61B 1/303* (2006.01)
  *A61B 17/04* (2006.01)
  *A61B 1/00* (2006.01)
  *A61B 1/06* (2006.01)
  *A61B 17/00* (2006.01)

(52) U.S. Cl.
  CPC .......... *A61B 1/0623* (2013.01); *A61B 1/0684* (2013.01); *A61B 1/303* (2013.01); *A61B 17/0483* (2013.01); *A61B 90/03* (2016.02); *A61B 90/361* (2016.02); *A61B 90/37* (2016.02); *A61B 2017/00424* (2013.01); *A61B 2017/00473* (2013.01); *A61B 2090/036* (2016.02)

(58) Field of Classification Search
  CPC ...... A61B 1/00179; A61B 2017/00473; A61B 90/36; A61B 2090/036; A61B 90/03; A61B 2017/00424; A61B 90/37; A61B 90/361; A61B 1/0623
  See application file for complete search history.

(56) References Cited

U.S. PATENT DOCUMENTS

| | | | |
|---|---|---|---|
| 4,198,982 A * | 4/1980 | Fortner | A61B 17/115 227/179.1 |
| 4,710,075 A * | 12/1987 | Davison | A61B 17/16 33/512 |
| 4,877,037 A * | 10/1989 | Ko | A61B 10/0291 600/569 |
| 5,409,496 A | 4/1995 | Rowden | |
| 5,421,346 A | 6/1995 | Sanyal | |
| 5,792,053 A | 8/1998 | Skladnev et al. | |
| 8,292,901 B2 | 10/2012 | Auerbach et al. | |
| 8,460,209 B2 | 6/2013 | Klein | |
| 8,976,363 B2 | 3/2015 | Bendall et al. | |
| 2003/0187334 A1 * | 10/2003 | Biswas | A61B 17/4241 600/227 |
| 2005/0137557 A1 | 6/2005 | Swiecicki et al. | |
| 2008/0221590 A1 | 9/2008 | Ikeda et al. | |
| 2009/0204126 A1 | 8/2009 | Le | |
| 2010/0106163 A1 | 4/2010 | Blair et al. | |
| 2010/0168784 A1 | 7/2010 | Pustinik | |
| 2010/0274087 A1 * | 10/2010 | Diolaiti | A61B 1/00087 600/118 |
| 2012/0016185 A1 * | 1/2012 | Sherts | A61B 17/12099 600/37 |
| 2012/0203244 A1 | 8/2012 | Mcdonald et al. | |
| 2012/0289585 A1 | 11/2012 | Ouyang | |
| 2012/0289858 A1 * | 11/2012 | Ouyang | A61B 10/0275 600/562 |
| 2012/0330324 A1 | 12/2012 | Sauer | |
| 2013/0072749 A1 * | 3/2013 | Fairneny | A61B 17/02 600/37 |
| 2013/0197537 A1 | 8/2013 | Faimeny | |
| 2015/0005780 A1 | 1/2015 | Einarsson | |

OTHER PUBLICATIONS

Richard M. Lebovitz, Jeffrey N. Fredman, and Jeffrey B. Robertson, Ex parte Mark Edmund Richey Decision on Appeal, Jun. 19, 2018. Appeal 2017-006891, U.S. Appl. No. 13/852,784, Technology Center 3700.

* cited by examiner

VAGINAL SURGICAL APPARATUS

PRIORITY CLAIM

This application is a continuation of U.S. non-provisional patent application Ser. No. 15/208,867 filed Jul. 13, 2016, which is a continuation of Ser. No. 15/179,215 filed Jun. 10, 2016, which application is (a) a non-provisional patent application of U.S. provisional patent application 62/174,127 filed Jun. 11, 2015; U.S. provisional patent application 62/193,721 filed Jul. 17, 2015; U.S. provisional patent application 62/252,810 filed Nov. 9, 2015; U.S. provisional patent application 62/257,090 filed Nov. 18, 2015; U.S. provisional patent application 62/265,038 filed Dec. 9, 2015; and U.S. provisional patent application 62/312,069 filed Mar. 23, 2016; (b) a continuation-in-part of U.S. non-provisional patent application Ser. No. 13/852,784 filed May 31, 2013; and (c) a continuation-in-part of U.S. nonprovisional patent application Ser. No. 14/971,512 filed Dec. 16, 2015.

This application claims the benefit of and/or priority to each of the foregoing patent applications and any and all parent, grandparent, and great-grandparent applications thereof. The foregoing patent applications are incorporated by reference in their entirety as if fully set forth herein.

FIELD OF THE INVENTION

This invention relates generally to a medical device, and more specifically, to a vaginal surgical apparatus.

SUMMARY

This invention relates generally to a medical device, and more specifically, to a vaginal surgical apparatus. In one embodiment, an apparatus includes, but is not limited to, an elongated handle portion; a vaginal manipulator probe that is at least partly insertable into a vagina, the vaginal manipulator probe extending from the elongated handle portion and including an arcuate end portion, the arcuate end portion including an aperture for accommodating a cervix; and a disk that is movable along at least a portion of a length of the vaginal manipulator probe, the disk including a locking mechanism to releasably secure the disk in position to limit vaginal insertion depth of the vaginal manipulator probe. In another embodiment, an apparatus includes, but is not limited to, an elongated handle portion that includes a first bollard tab and a second bollard tab for releasably securing a suture; a vaginal manipulator probe extending from the elongated handle portion and including an arcuate end portion having an oval-cross sectional shape and having an aperture channel for accommodating a cervix; and a disk that is movable along at least a portion of a length of the vaginal manipulator probe, the disk including a locking mechanism to releasably secure the disk in position to limit vaginal insertion depth of the vaginal manipulator probe. In a further embodiment, an apparatus includes, but is not limited to, an elongated handle portion that includes a first bollard tab and a second bollard tab for releasably securing a suture; a vaginal manipulator probe extending from the elongated handle portion and including an arcuate end portion having an oval-cross sectional shape and having an aperture channel for accommodating a cervix, the arcuate end portion terminating to a bullous tip; a disk including a sleeve and shoulder, the disk being movable along at least a portion of a length of the vaginal manipulator probe; and a spring loaded latch associated with the disk to releasably secure the disk in position along a length of the vaginal manipulator probe to limit vaginal insertion depth. In yet an additional embodiment, an apparatus includes, but is not limited to, a handle portion; a vaginal manipulator probe that is at least partly insertable into a vagina, the vaginal manipulator probe extending from the handle portion and including an arcuate end portion, the arcuate end portion including an channel for accommodating a cervix; one or more LED lights disposed on the vaginal manipulator probe for illuminating vaginal tissue; at least one camera positioned with a field of view of the channel to permit visualization of a cervix relative to the channel; at least one battery receptacle within the handle portion; at least one button or switch operable to control operation of the one or more LED lights; at least one communication link for transferring image data to at least one display unit, the at least one communication link being either a wired communication link or a wireless communication link; and a disk that is movable along at least a portion of a length of the vaginal manipulator probe, the disk including a locking mechanism to releasably secure the disk in position along the portion of the length of the vaginal manipulator probe to limit vaginal insertion depth of the vaginal manipulator probe.

BRIEF DESCRIPTION OF THE DRAWINGS

Embodiments of the present invention are described in detail below with reference to the following drawings.

DETAILED DESCRIPTION

This invention relates generally to a medical device, and more specifically, to a vaginal surgical apparatus. Certain embodiments of the invention are set forth in the following description and in FIGS. 1-6 to provide a thorough understanding of such embodiments. The present invention may have additional embodiments, may be practiced without one or more of the details described for any particular described embodiment, or may have any detail described for one particular embodiment practiced with any other detail described for another embodiment.

Figure 1:
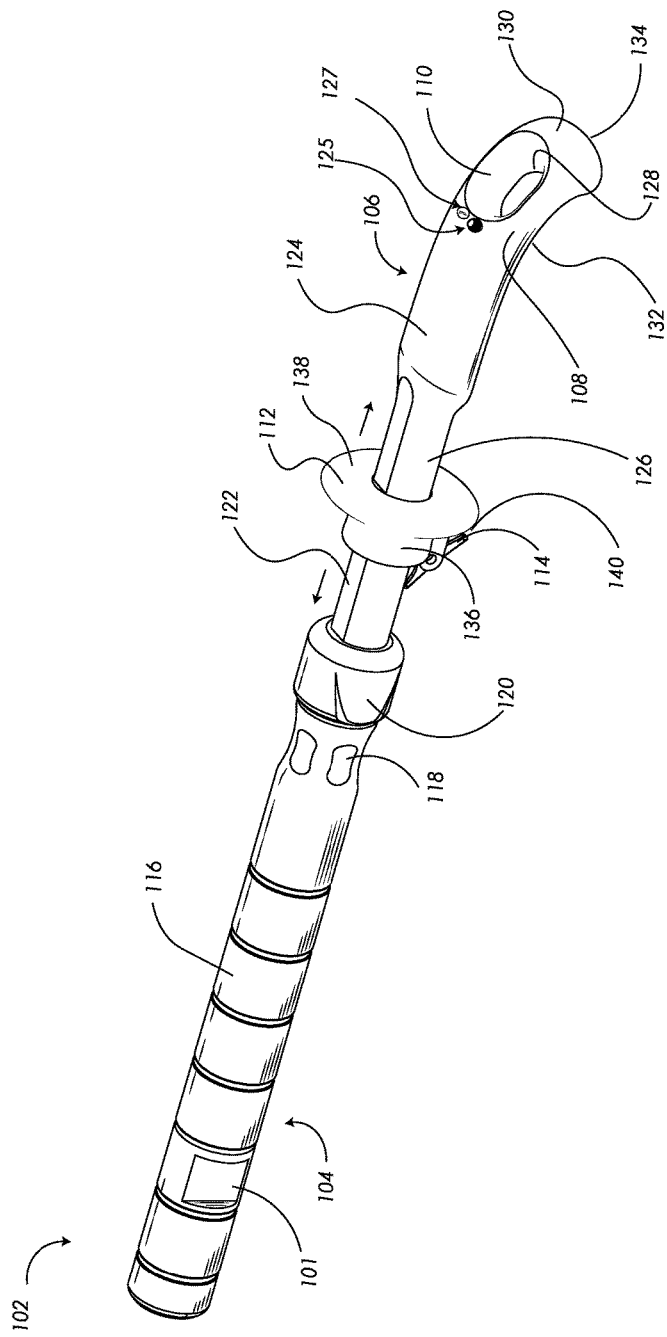
FIG. 1 is a top perspective view of a vaginal surgical apparatus, in accordance with an embodiment of the invention.

FIG. 1 is a top perspective view of a vaginal surgical apparatus, in accordance with an embodiment of the invention. In one embodiment, an apparatus 102 includes, but is not limited to, an elongated handle portion 104; a vaginal manipulator probe 106 that is at least partly insertable into a vagina, the vaginal manipulator probe 106 extending from the elongated handle portion 104 and including an arcuate end portion 108, the arcuate end portion 108 including an aperture 110 for accommodating a cervix; and a disk 112 that is movable along at least a portion of a length of the vaginal manipulator probe 106, the disk 112 including a locking mechanism 114 to releasably secure the disk 112 in position to limit vaginal insertion depth of the vaginal manipulator probe 106. In one particular embodiment, the elongated handle portion 104 is a cylindrical shaft 116. In another embodiment, the elongated handle portion 104 includes a recessed waist portion 118. In certain embodiments, the vaginal manipulator probe 106 is releasable from the elongated handle portion 104. Alternatively, in some embodiments, the vaginal manipulator probe 106 and the elongated handle portion 104 are a unitary structure. In one embodiment, the elongated handle portion 104 includes a first bollard tab 120 and a second bollard tab (not visible) opposite the first bollard tab 120 for releasably securing a suture. In further embodiments, the vaginal manipulator probe 106 has an oval cross-sectional shape along a length of a longitudinal axis of the vaginal manipulator probe 106. In one particular embodiment, the vaginal manipulator probe 106 includes a first portion 122 having a first cross-sectional width that flares to a second portion 124 having a second cross-sectional width that is greater than the first-cross-sectional width, wherein the first portion 122 and the second portion 124 have substantially similar cross-sectional heights. In some embodiments, the vaginal manipulator probe 106 includes a notch track (not visible) for interfacing with the locking mechanism 114 of the disk 112. In additional embodiments, the vaginal manipulator probe 106 includes a linear portion 126 that extends from the arcuate end portion 108. In one particular embodiment, the aperture 110 of the arcuate end portion 108 of the vaginal manipulator probe 106 extends as a channel 128 from a top surface 130 of the vaginal manipulator probe 106 through to a bottom surface 132 of the vaginal manipulator probe 106. In one embodiment, the aperture 110 is positioned approximately midway along a length of the arcuate end portion 108 of the vaginal manipulator probe 106. In other embodiments, the vaginal manipulator probe 106 includes an end portion 134 that curls to define a bullous tip (not visible). In one specific embodiment, the aperture 110 measures approximately 2 cm to 4 cm across and/or in length. In some embodiments, the disk 112 is movable along a portion of a length of the vaginal manipulator probe 106 having a notch track (not visible). In further embodiments, the disk 112 includes a sleeve portion 136 that circumscribes the vaginal manipulator probe 106. In other embodiments, the disk 112 includes a shoulder 138 that circumscribes the vaginal manipulator probe 106, the shoulder 138 being operable to rest against an outside surface of a vulva when the vaginal manipulator probe 106 is inserted within the vagina. In a further embodiment, the disk 112 includes a spring-loaded latch 140 that is tensionally biased against a notch track (not visible) of the vaginal manipulator probe 106.

In one embodiment, an apparatus 102 includes, but is not limited to, an elongated handle portion 104 that includes a first bollard tab 120 and a second bollard tab (not visible) for releasably securing a suture; a vaginal manipulator probe 106 extending from the elongated handle portion 104 and including an arcuate end portion 108 having an oval-cross sectional shape and having an aperture channel 110 for accommodating a cervix; and a disk 112 that is movable along at least a portion of a length of the vaginal manipulator probe 106, the disk 112 including a locking mechanism 114 to releasably secure the disk 112 in position to limit vaginal insertion depth of the vaginal manipulator probe 106.

In another embodiment, an apparatus 102 includes, but is not limited to, an elongated handle portion 104 that includes a first bollard tab 120 and a second bollard tab (not visible) for releasably securing a suture; a vaginal manipulator probe 106 extending from the elongated handle portion 104 and including an arcuate end portion 108 having an oval-cross sectional shape and having an aperture channel 110 for accommodating a cervix, the arcuate end portion 108 terminating to a bullous tip (not visible); a disk 112 including a sleeve 136 and shoulder 138, the disk 112 being movable along at least a portion of a length of the vaginal manipulator probe 106; and a spring loaded latch 140 associated with the disk 112 to releasably secure the disk 112 in position along a length of the vaginal manipulator probe 106 to limit vaginal insertion depth.

In one embodiment, the elongated handle portion 104 includes a notch 101 on opposing sides to define a surface for securing the apparatus 102, such as using a locking mechanism, clamp, clasp associated with a table or resting surface.

In some embodiments, the cylindrical shaft 116 is non-cylindrical such as oval, square, triangular, or irregular in shape. In other embodiments, the cylindrical shaft 116 is non-linear, such as including a bend or curve along its length. In further embodiments, the notch 101 is omitted or substituted with a hole, channel, or protrusion. Alternatively, a clamp, clasp, or other securing mechanism can be included with the cylindrical shaft 116 to facilitate securing the apparatus 102 to a table, support, stand, or other structure. In some embodiments, the recessed waist 118 is omitted or can be duplicated at different positions along a length of the cylindrical shaft to provide additional grip points. In certain embodiments, the first bollard tab 120 and the second bollard tab 202 can be omitted or positionable on a rotatably lockable or slidable sleeve that permits different alignment/positioning. In an additional embodiment, the cylindrical shaft 116 can be tapped with threads to permit screwing and unscrewing of the vaginal manipulator probe 106. Alternatively, the cylindrical shaft 116 can include a tapered, friction, bearing, post, groove, or other locking mechanism for removably securing the vaginal manipulator probe 106.

In an additional embodiment, the vaginal manipulator probe 106 is arcuate along a substantially entire length (e.g., curved along a majority of the length without having the linear portion 126). The arcuate end portion 108 can have a curvature as depicted or alternatively can be curved to a greater or lesser extent as desired to accommodate the vaginal anatomy. In certain embodiments, the arcuate end portion 108 can include an adjustable curvature to permit point-of-use adjustment by a health provider or doctor. Alternatively, the vaginal manipulator probe 106 can be substantially linear along its substantially entire length (e.g., not including the arcuate end portion 108). In certain embodiments, the linear portion 126 and the arcuate end portion 108 have a circular, oval, square, triangular, irregular, or other similar cross-sectional shape, which may be the same or different between the two. In another embodiment, the linear portion 126 and the arcuate end portion 108 have substantially similar widths or heights or can have differing widths or heights. In other embodiments, the arcuate end portion 108 can include a larger or smaller flare from the linear portion 126 to define a wider or narrower shape. In some embodiments, the arcuate end portion 108 can have a varying diameter, height, or cross sectional shape along its length. In other embodiments, the end portion 134 is flat, curved, pointed, conical, or has another similar shape. In a further embodiment, the aperture 110 can be a surface indentation or can extend fully or partly through the vaginal manipulator probe 106. In one particular embodiment, walls of the aperture 110 are tapered in or out to define a surface for accommodating various anatomical features. The aperture 110 can be square, rectangular, oval, circular, triangular, or another similar shape. The aperture 110 can be positioned further towards the end portion 134 or further towards the linear portion 126. The aperture 110 can extend further along a length of the arcuate end portion 108 or can be shortened. Additionally, in some embodiments, the aperture 110 can be adjustable in width, height, depth, diameter, or shape. In other embodiments, the disk 112 can include a larger or a smaller diameter shoulder 138. The sleeve portion 136 can be omitted or extended further forward or aft to cover more of the linear portion 126. The linear portion 126 can include measurement markings to indicate a distance of insertion from the end portion 134. The locking mechanism 114 can be omitted or substituted, such as with a threaded disk that rotates, a pin and hole, a screw and track, or another similar structure.

In additional embodiments, the apparatus 102 includes one or more cameras 127 positioned at one or more points to provide visual feedback, such as proximate the end portion 134, along a length of the arcuate end portion 108, or proximate the aperture 110, as depicted. In certain embodiments, the one or more cameras 127 can be disposed on a top surface 130 of the vaginal manipulator probe 106 or on a bottom surface 132 of the vaginal manipulator probe or even on either side of the vaginal manipulator probe 106. In one particular embodiment, the one or more cameras 127 are disposed on a top surface 130 and are angled to permit visualization of the aperture 110 relative to the cervix to facilitate proper positioning of the cervix within the aperture 110. Alternatively, the one or more cameras 127 can be positioned along the vaginal manipulator probe 106—either on the linear portion 126 or the arcuate end portion 108—permitting visualization of the vaginal manipulator probe 106 relative to various vaginal anatomical structures and/or one or more needles or surgical tools. In certain embodiments, the one or more LED lights 125 are positioned to illuminate the aperture 110 to facilitate imaging using the one or more cameras 127. The one or more LED lights 125 are depicted as being proximate the one or more cameras 127 and positioned to illuminate the aperture 110. However, the one or more LED lights 125 are not limited to being positioned as depicted. For example, in certain embodiments, the apparatus 102 includes one or more LED lights 125 surrounding the aperture 110, which one or more LED lights 125 emit light that is detectable through the tissue of a cervix and trans-illuminate tissue of the vagina. This positioning of the one or more LED lights 125 facilitates correct positioning of the vaginal manipulator probe 106 relative to the cervix. The one or more LED lights 125 can be disposed around the aperture 110 on the inside diameter walls or near a lip on the top surface 130 or the bottom surface 132. The one or more LED lights 125 can be positioned anywhere on the arcuate end portion 108 or the linear portion 126. Alternatively, the one or more LED lights 125 can be disposed anywhere along the vaginal manipulator probe 106 or even along the elongated handle portion 104. Thus, in certain embodiments, the one or more cameras 127 at a vantage point to visualize the aperture 110, with the one or more LED lights 125 adjacent. Another location for the one or more LED lights 125 is on the top of a cervical "ring" in a series all around the aperture 110, which would be in direct contact with the vagina where the vagina attaches to the cervix, thereby trans-illuminating the vagina at that junction for the surgeon/health provider to see from an abdominal perspective. Alternatively, the one or more LED lights 125 could be in a small series of 3 or 4 lights at the junction of the vaginal manipulator probe 106 where it transitions to the aperture 110. Additionally, the vaginal manipulator probe 106 is configured to change or emit color/light, such as using one or more internal or externally mounted LED lights 125 to provide contrast relative to tissue or blood. Batteries in any of these embodiments can be disposed within the elongated handle portion 104.

In one particular embodiment, a display screen is included to permit display of one or more images/video captured using the one or more cameras 127. The display screen can be integrated or coupled to the elongated handle portion 104 or can be detachable and removably couplable to the elongated handle portion. The display screen can be pivoted, angled, shifted, moved to permit visualization by a healthcare provider during application. The display screen can be disposable or reusable. The display screen can include or be associated with one or more buttons or switches to permit control of the one or more LED lights 125 or the one or more cameras 127. For instance, the one or more LED lights 125 can be turned on or off or have varying intensity or color. Additionally, the one or more cameras 127 can be robotically moved, angled, shifted or can even enable zoom, image, video, contrast, etc. changes.

In further embodiments, the arcuate end portion 108 includes one or more indentations or grooves on its surface to backstop a needle, similar in function to a thimble. In some embodiments, one or more physiological sensors are disposed on a surface of the apparatus 102 or internally of the apparatus 102, such physiological sensors can provide data feedback regarding temperature, chemical, coloration, or other similar information. In certain embodiments, the apparatus 102 includes an internal conduit that exits via the end portion 134 or via one or more pores in the vaginal manipulator probe 106 for medication or fluid delivery. The internal conduit can include an attachment point in the elongated handle portion for coupling with a catheter or other conduit for receiving fluids or medication. Alternatively, the internal conduct can extend from a refillable reservoir disposed within the apparatus 102 for containing fluid or medication. The apparatus 102 can further include a processor, computer readable storage, buttons, switches, and/or one or more wireless or wired communication units to enable automatic, programmed, remote, or local control of the operations, such as light, drug administration, sensors, data collection and transmission, size or shape or curvature adjustments, or other similar operations.

Figure 2:
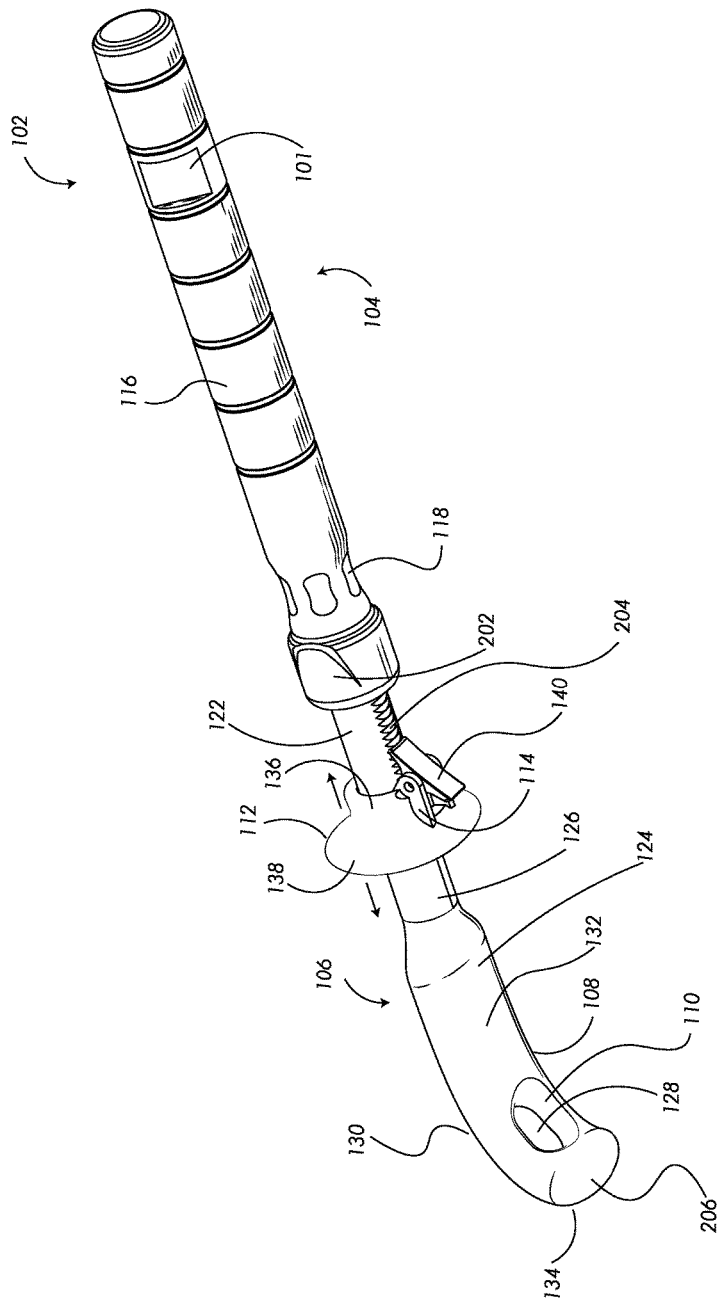
FIG. 2 is a bottom perspective view of a vaginal surgical apparatus, in accordance with an embodiment of the invention.

FIG. 2 is a bottom perspective view of a vaginal surgical apparatus, in accordance with an embodiment of the invention. In one embodiment, an apparatus 102 includes, but is not limited to, an elongated handle portion 104; a vaginal manipulator probe 106 that is at least partly insertable into a vagina, the vaginal manipulator probe 106 extending from the elongated handle portion 104 and including an arcuate end portion 108, the arcuate end portion 108 including an aperture 110 for accommodating a cervix; and a disk 112 that is movable along at least a portion of a length of the vaginal manipulator probe 106, the disk 112 including a locking mechanism 114 to releasably secure the disk 112 in position to limit vaginal insertion depth of the vaginal manipulator probe 106. In one particular embodiment, the elongated handle portion 104 is a cylindrical shaft 116. In another embodiment, the elongated handle portion 104 includes a recessed waist portion 118. In certain embodiments, the vaginal manipulator probe 106 is releasable from the elongated handle portion 104. Alternatively, in some embodiments, the vaginal manipulator probe 106 and the elongated handle portion 104 are a unitary structure. In one embodiment, the elongated handle portion 104 includes a first bollard tab (not visible) and a second bollard tab 202 opposite the first bollard tab for releasably securing a suture. In further embodiments, the vaginal manipulator probe 106 has an oval cross-sectional shape along a length of a longitudinal axis of the vaginal manipulator probe 106. In one particular embodiment, the vaginal manipulator probe 106 includes a first portion 122 having a first cross-sectional width that flares to a second portion 124 having a second cross-sectional width that is greater than the first-cross-sectional width, wherein the first portion 122 and the second portion 124 have substantially similar cross-sectional heights. In some embodiments, the vaginal manipulator probe 106 includes a notch track 204 for interfacing with the locking mechanism 114 of the disk 112. In additional embodiments, the vaginal manipulator probe 106 includes a linear portion 126 that extends from the arcuate end portion 108. In one particular embodiment, the aperture 110 of the arcuate end portion 108 of the vaginal manipulator probe 106 extends as a channel 128 from a top surface 130 of the vaginal manipulator probe 106 through to a bottom surface 132 of the vaginal manipulator probe 106. In one embodiment, the aperture 110 is positioned approximately midway along a length of the arcuate end portion 108 of the vaginal manipulator probe 106. In other embodiments, the vaginal manipulator probe 106 includes an end portion 134 that curls to define a bullous tip 206. In one specific embodiment, the aperture 110 measures approximately 2 cm to 4 cm across and/or in length. In some embodiments, the disk 112 is movable along a portion of a length of the vaginal manipulator probe 106 having a notch track 204. In further embodiments, the disk 112 includes a sleeve portion 136 that circumscribes the vaginal manipulator probe 106. In other embodiments, the disk 112 includes a shoulder 138 that circumscribes the vaginal manipulator probe 106, the shoulder 138 being operable to rest against an outside surface of a vulva when the vaginal manipulator probe 106 is inserted within the vagina. In a further embodiment, the disk 112 includes a spring-loaded latch 140 that is tensionally biased against a notch track 204 of the vaginal manipulator probe 106.

In one embodiment, an apparatus 102 includes, but is not limited to, an elongated handle portion 104 that includes a first bollard tab (not visible) and a second bollard tab 202 for releasably securing a suture; a vaginal manipulator probe 106 extending from the elongated handle portion 104 and including an arcuate end portion 108 having an oval-cross sectional shape and having an aperture channel 110 for accommodating a cervix; and a disk 112 that is movable along at least a portion of a length of the vaginal manipulator probe 106, the disk 112 including a locking mechanism 114 to releasably secure the disk 112 in position to limit vaginal insertion depth of the vaginal manipulator probe 106.

In another embodiment, an apparatus 102 includes, but is not limited to, an elongated handle portion 104 that includes a first bollard tab (not visible) and a second bollard tab 202 for releasably securing a suture; a vaginal manipulator probe 106 extending from the elongated handle portion 104 and including an arcuate end portion 108 having an oval-cross sectional shape and having an aperture channel 110 for accommodating a cervix, the arcuate end portion 108 terminating to a bullous tip 206; a disk 112 including a sleeve 136 and shoulder 138, the disk 112 being movable along at least a portion of a length of the vaginal manipulator probe 106; and a spring loaded latch 140 associated with the disk 112 to releasably secure the disk 112 in position along a length of the vaginal manipulator probe 106 to limit vaginal insertion depth.

Figure 3:
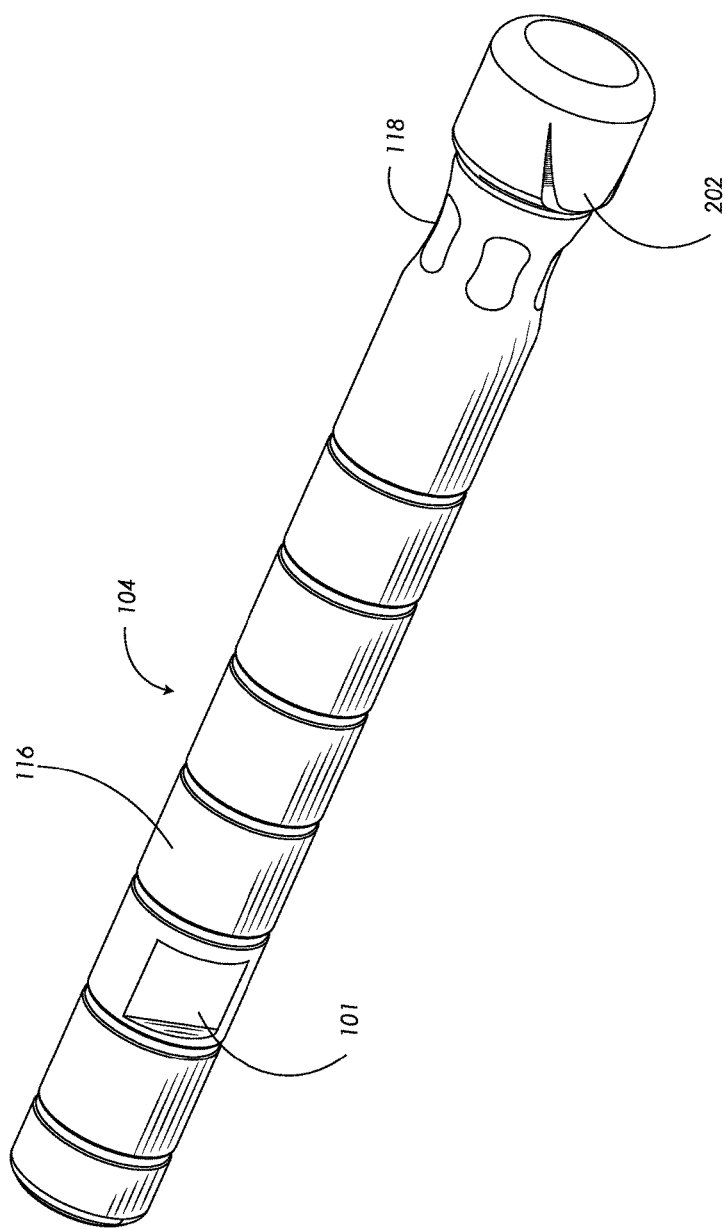
FIG. 3 is a perspective view of a handle portion of a vaginal surgical apparatus, in accordance with an embodiment of the invention.

FIG. 3 is a perspective view of a handle portion of a vaginal surgical apparatus, in accordance with an embodiment of the invention. In one embodiment, the elongated handle portion 104 is a cylindrical shaft 116. In another embodiment, the elongated handle portion 104 includes a recessed waist portion 118. In certain embodiments, the elongated handle portion 104 is releasable from the vaginal manipulator probe (not shown). Alternatively, in some embodiments, the vaginal manipulator probe (not shown) and the elongated handle portion 104 are a unitary structure. In one embodiment, the elongated handle portion 104 includes a first bollard tab (not visible) and a second bollard tab 202 opposite the first bollard tab for releasably securing a suture. In another embodiment, the elongated handle portion 104 includes a notch 101 on opposing sides to define a planar surface for accommodating a clasp, clamp, or other securing mechanism to hold the apparatus in position.

Figure 4:
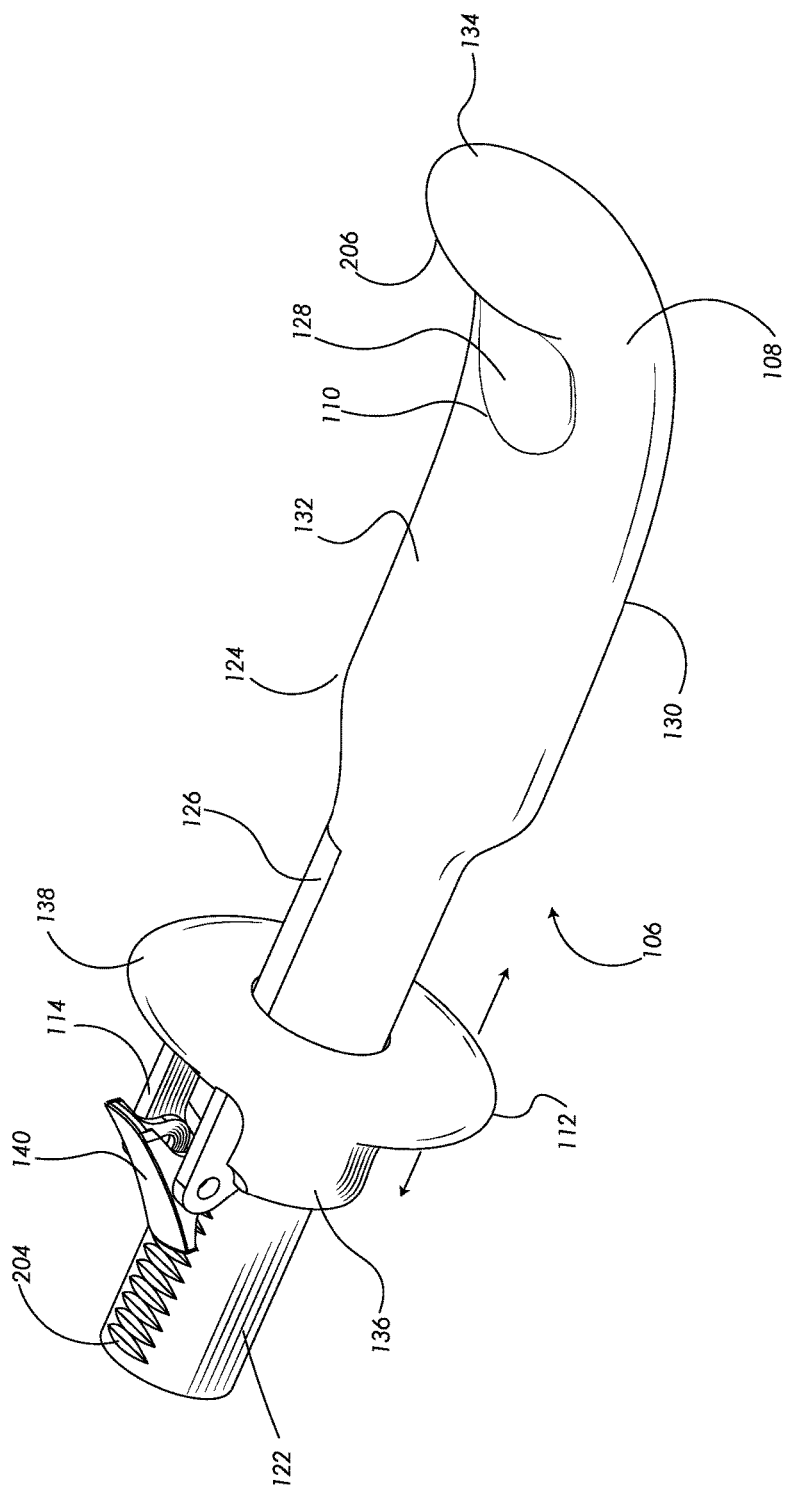
FIG. 4 is a perspective view of a vaginal manipulator probe of a vaginal surgical apparatus, in accordance with an embodiment of the invention.

FIG. 4 is a perspective view of a vaginal manipulator probe of a vaginal surgical apparatus, in accordance with an embodiment of the invention. In one embodiment, the vaginal manipulator probe 106 has an oval cross-sectional shape along a length of a longitudinal axis of the vaginal manipulator probe 106. In one particular embodiment, the vaginal manipulator probe 106 includes a first portion 122 having a first cross-sectional width that flares to a second portion 124 having a second cross-sectional width that is greater than the first-cross-sectional width, wherein the first portion 122 and the second portion 124 have substantially similar cross-sectional heights. In some embodiments, the vaginal manipulator probe 106 includes a notch track 204 for interfacing with the locking mechanism 114 of the disk 112. In additional embodiments, the vaginal manipulator probe 106 includes a linear portion 126 that extends from the arcuate end portion 108. In one particular embodiment, the aperture 110 of the arcuate end portion 108 of the vaginal manipulator probe 106 extends as a channel 128 from a top surface 130 of the vaginal manipulator probe 106 through to a bottom surface 132 of the vaginal manipulator probe 106. In one embodiment, the aperture 110 is positioned approximately midway along a length of the arcuate end portion 108 of the vaginal manipulator probe 106. In other embodiments, the vaginal manipulator probe 106 includes an end portion 134 that curls to define a bullous tip 206. In one specific embodiment, the aperture 110 measures approximately 2 cm to 4 cm across and/or in length. In some embodiments, the disk 112 is movable along a portion of a length of the vaginal manipulator probe 106 having a notch track 204. In further embodiments, the disk 112 includes a sleeve portion 136 that circumscribes the vaginal manipulator probe 106. In other embodiments, the disk 112 includes a shoulder 138 that circumscribes the vaginal manipulator probe 106, the shoulder 138 being operable to rest against an outside surface of a vulva when the vaginal manipulator probe 106 is inserted within the vagina. In a further embodiment, the disk 112 includes a spring-loaded latch 140 that is tensionally biased against a notch track 204 of the vaginal manipulator probe 106.

Figure 5:
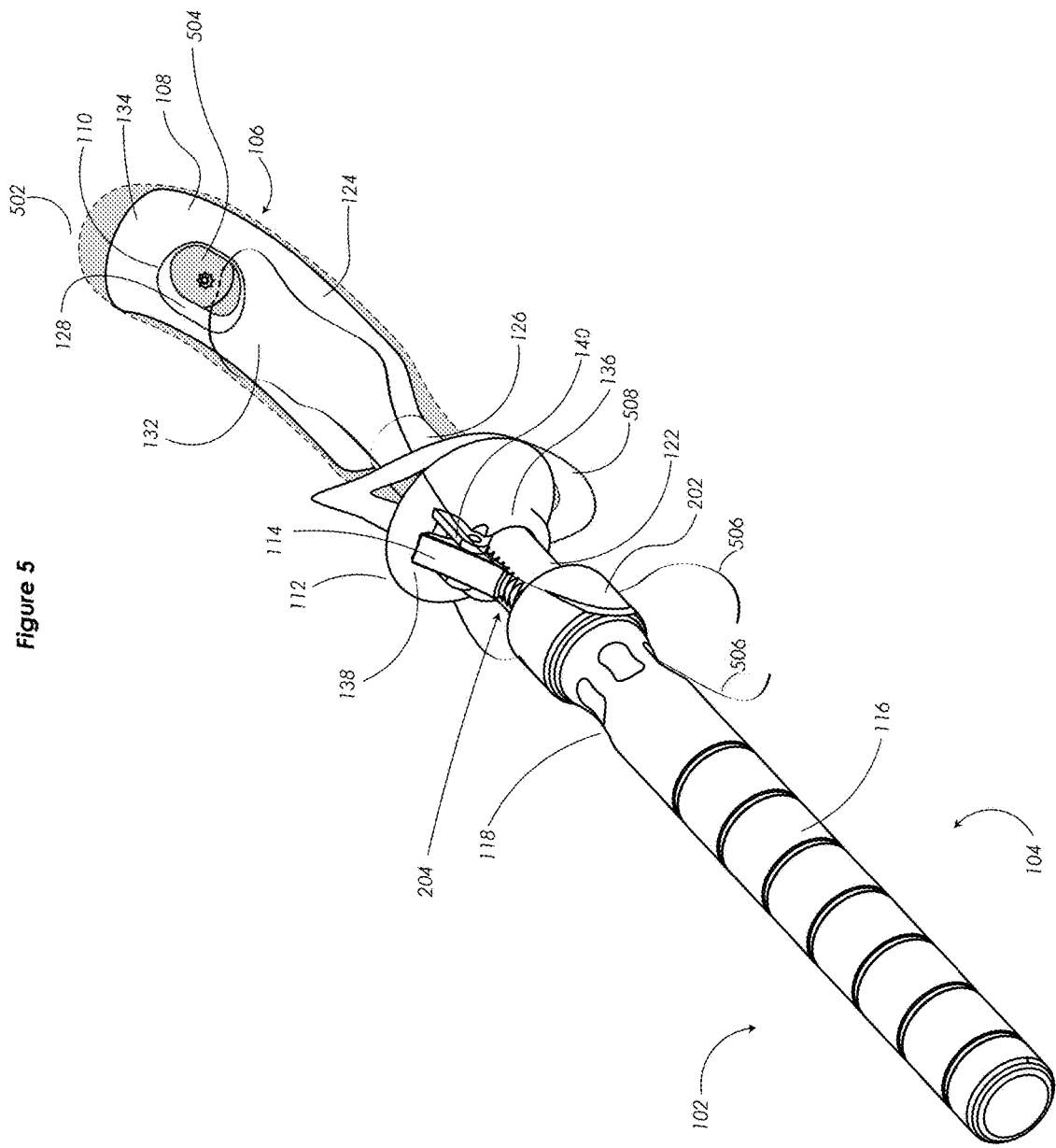
FIG. 5 is a perspective view of a vaginal manipulator probe of a vaginal surgical apparatus inserted into a vaginal space, in accordance with an embodiment of the invention.

FIG. 5 is a perspective view of a vaginal manipulator probe of a vaginal surgical apparatus inserted into a vaginal space, in accordance with an embodiment of the invention. In one embodiment, an apparatus 102 includes, but is not limited to, an elongated handle portion 104; a vaginal manipulator probe 106 that is at least partly insertable into a vagina 502, the vaginal manipulator probe 106 extending from the elongated handle portion 104 and including an arcuate end portion 108, the arcuate end portion 108 including an aperture 110 for accommodating a cervix 504; and a disk 112 that is movable along at least a portion of a length of the vaginal manipulator probe 106, the disk 112 including a locking mechanism 114 to releasably secure the disk 112 in position to limit vaginal insertion depth of the vaginal manipulator probe 106. In one particular embodiment, the elongated handle portion 104 is a cylindrical shaft 116. In another embodiment, the elongated handle portion 104 includes a recessed waist portion 118. In certain embodiments, the vaginal manipulator probe 106 is releasable from the elongated handle portion 104. Alternatively, in some embodiments, the vaginal manipulator probe 106 and the elongated handle portion 104 are a unitary structure. In one embodiment, the elongated handle portion 104 includes a first bollard tab (not visible) and a second bollard tab 202 opposite the first bollard tab for releasably securing a suture 506. In further embodiments, the vaginal manipulator probe 106 has an oval cross-sectional shape along a length of a longitudinal axis of the vaginal manipulator probe 106. In one particular embodiment, the vaginal manipulator probe 106 includes a first portion 122 having a first cross-sectional width that flares to a second portion 124 having a second cross-sectional width that is greater than the first-cross-sectional width, wherein the first portion 122 and the second portion 124 have substantially similar cross-sectional heights. In some embodiments, the vaginal manipulator probe 106 includes a notch track 204 for interfacing with the locking mechanism 114 of the disk 112. In additional embodiments, the vaginal manipulator probe 106 includes a linear portion 126 that extends from the arcuate end portion 108. In one particular embodiment, the aperture 110 of the arcuate end portion 108 of the vaginal manipulator probe 106 extends as a channel 128 from a top surface (not visible) of the vaginal manipulator probe 106 through to a bottom surface 132 of the vaginal manipulator probe 106. In one embodiment, the aperture 110 is positioned approximately midway along a length of the arcuate end portion 108 of the vaginal manipulator probe 106. In other embodiments, the vaginal manipulator probe 106 includes an end portion 134 that curls to define a bullous tip. In one specific embodiment, the aperture 110 measures approximately 2 cm to 4 cm across and/or in length. In some embodiments, the disk 112 is movable along a portion of a length of the vaginal manipulator probe 106 having the notch track 204. In further embodiments, the disk 112 includes a sleeve portion 136 that circumscribes the vaginal manipulator probe 106. In other embodiments, the disk 112 includes a shoulder 138 that circumscribes the vaginal manipulator probe 106, the shoulder 138 being operable to rest against an outside surface of a vulva 508 when the vaginal manipulator probe 106 is inserted within the vagina 502. In a further embodiment, the disk 112 includes a spring loaded latch 140 that is tensionally biased against the notch track 204 of the vaginal manipulator probe 106.

In one embodiment, an apparatus 102 includes, but is not limited to, an elongated handle portion 104 that includes a first bollard tab (not visible) and a second bollard tab 202 for releasably securing a suture 506; a vaginal manipulator probe 106 extending from the elongated handle portion 104 and including an arcuate end portion 108 having an oval-cross sectional shape and having an aperture channel 110 for accommodating a cervix 504; and a disk 112 that is movable along at least a portion of a length of the vaginal manipulator probe 106, the disk 112 including a locking mechanism 114 to releasably secure the disk 112 in position to limit vaginal insertion depth of the vaginal manipulator probe 106.

In another embodiment, an apparatus 102 includes, but is not limited to, an elongated handle portion 104 that includes a first bollard tab (not visible) and a second bollard tab 202 for releasably securing a suture 506; a vaginal manipulator probe 106 extending from the elongated handle portion 104 and including an arcuate end portion 108 having an oval-cross sectional shape and having an aperture channel 110 for accommodating a cervix 504, the arcuate end portion 108 terminating to a bullous tip; a disk 112 including a sleeve 136 and shoulder 138, the disk 112 being movable along at least a portion of a length of the vaginal manipulator probe 106; and a spring loaded latch 140 associated with the disk 112 to releasably secure the disk 112 in position along a length of the vaginal manipulator probe 106 to limit vaginal insertion depth.

Figure 6:
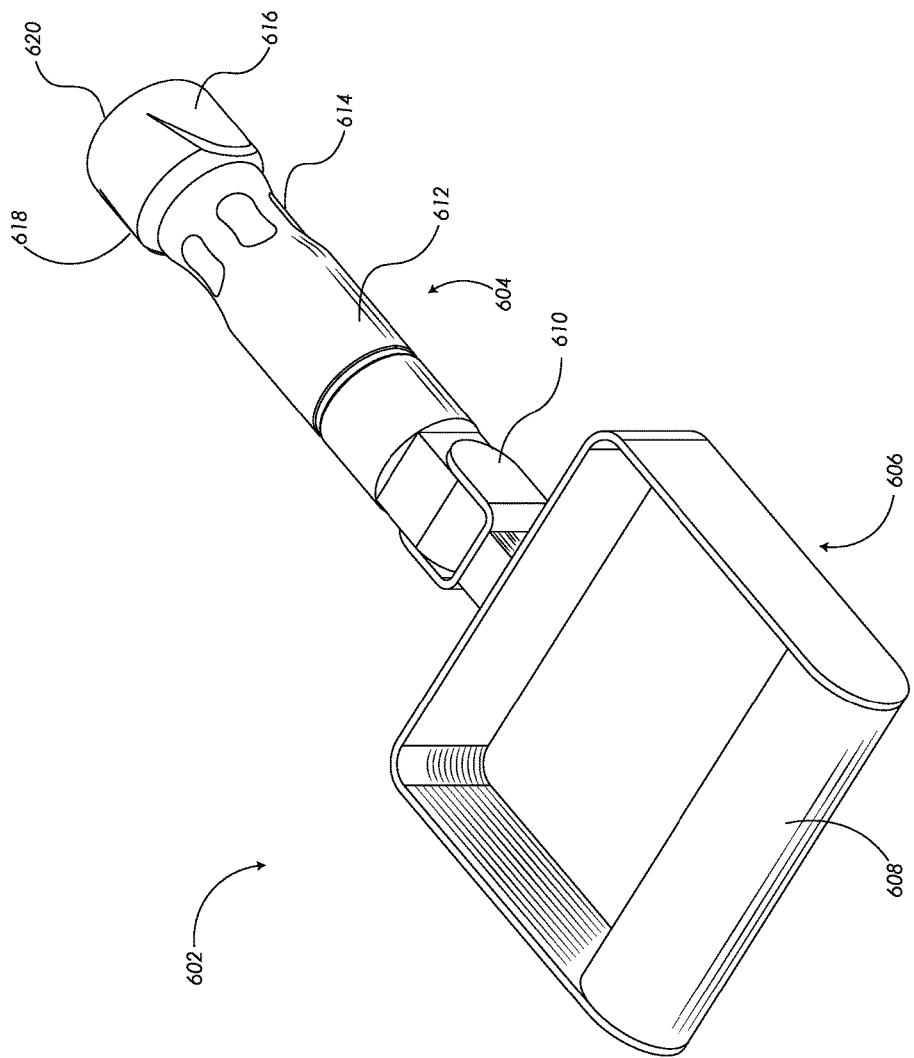
FIG. 6 is a perspective view of a movable handle of a vaginal surgical apparatus, in accordance with an embodiment of the invention.

FIG. 6 is a perspective view of a movable handle of a vaginal surgical apparatus, in accordance with an embodiment of the invention. In one embodiment, a movable handle 602 includes an elongated portion 604 movably coupled to a handle portion 606 via an articulating joint 610. The handle portion 606 includes a grip. The elongated portion 604 includes a shaft with a recessed waist 614 terminating at a vaginal manipulator probe attachment end 620. The shaft 612 can include a first bollard tab 616 and a second bollard tab 618 for securing one or more sutures (not visible). Accordingly, the movable handle 602 can be used in conjunction with various embodiments disclosed herein to provide an alternative handle structure for manipulating a vaginal manipulator probe 106.

In certain embodiments, wherein the elongated portion 604 is a cylindrical shaft. In other embodiments, the elongated portion 604 includes a recessed waist 614 for accommodating a thumb. In other embodiments, the elongated portion 604 is releasable from a vaginal manipulator probe 106. In further embodiments, the elongated portion 604 and a vaginal manipulator probe are provided as a unitary structure.

In some embodiments, the handle portion 606 rotates and/or pivots relative to the elongated portion 604. The articulating joint 610 can permit movement in one, two, or three directions, such as being capable of adjustably extending from the elongated portion 604. In certain embodiments, the articulating joint is lockable in one or more positions via friction, a locking mechanism (e.g., pin, screw, jam nut, or similar structure), or is freely movable. In other embodiments, the handle portion 606 includes a shaft grip, a knob, one or more finger holes, or a differently configured grip 608 (e.g., narrower, wider, thicker, thinner, etc.).

In further embodiments, the shaft 612 is differently configured, such as shorter, longer, wider, non-linear, squared, or the like. The shaft 612 can be removably coupled to the vaginal manipulator probe as discussed herein, or can be part of a unitary structure with the vaginal manipulator probe. The recessed waist 614 can be differently positioned, duplicated, longer, deeper, shorter, or even omitted. The first and second bollard tabs 616 and 618 can be omitted or differently positioned, such as on a rotatable or movable sleeve.

In one particular embodiment, a movable handle 602 is similar to the part that you hold on a child's red wagon. The movable handle 602 can be an option to slip onto or couple with the vaginal manipulator probe 106. The movable handle 602 can be secured in place with a spring-loaded button or other simple device, and have a short extension which swivels in the anterior-posterior plane only allowing several handle positions, perhaps three. The movable handle 602 includes an opening (where the surgeon's fingers would be located) which enables access to the anal canal with a separate probe.

In one other particular embodiment, the elongated portion 104 or 604 has a bend or is offset from a midline to define a space that accommodates a rectal probe (which extending straight out of the anus) without conflicting with each other. This allows for easier positioning of the apparatus. It would also allow easier positioning of the apparatus 102 while concurrently suing a rectal probe—maintaining the apparatus 102 in the midline, rather than having it at an eccentric angle.

While preferred and alternate embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. An apparatus comprising:
    an elongated handle portion having a first end and a second end;
    a vaginal manipulator probe that is at least partly insertable into a vagina, the vaginal manipulator probe extending from the elongated handle portion and including an arcuate end portion that is curved away from a longitudinal axis of the vaginal manipulator probe to a bullous tip, the arcuate end portion including a channel that has a diameter that accommodates a cervix therewithin, the bullous tip defined by distention that increases a cross-sectional height between a bottom surface and a top surface of the vaginal manipulator probe; and
    a disk that is movable along at least a portion of a length of the vaginal manipulator probe, the disk including a locking mechanism to releasably secure the disk in position to limit vaginal insertion depth of the vaginal manipulator probe.

2. The apparatus of claim 1, wherein the locking mechanism comprises a latch on the disk that secures to one or more notches along a length of the vaginal manipulator probe.

3. The apparatus of claim 1, further comprising:
    a nut that rotates about at least some threads on the vaginal manipulator probe to limit movement of the disk; and
    a locking mechanism to removably secure the nut at one or more positions along a length of the vaginal manipulator probe.

4. The apparatus of claim 1, wherein the vaginal manipulator probe includes a first portion having a notch track for interfacing with the locking mechanism on the disk.

5. The apparatus of claim 1, wherein the vaginal manipulator probe and the elongated handle portion are a unitary structure.

6. The apparatus of claim 1, wherein the elongated handle portion includes a first bollard tab and a second bollard tab opposite the first bollard tab for releasably securing one or more ends of a suture.

7. The apparatus of claim 1, further comprising:
    a robotic arm, wherein the elongated handle portion is removably securable to the robotic arm.

8. The apparatus of claim 1, wherein the vaginal manipulator probe has a circular cross-sectional shape at its proximal end that becomes a flattened oval cross-sectional shape toward its distal end such that a widest portion of the flattened oval cross-sectional shape is approximately in a transverse plane when inserted into a vagina.

9. The apparatus of claim 1, wherein the vaginal manipulator probe is releasable from the elongated handle portion.

10. The apparatus of claim 1, wherein the vaginal manipulator probe includes a surface coloration that contrasts with tissue.

11. The apparatus of claim 1, wherein an aperture of the arcuate end portion of the vaginal manipulator probe extends as a channel from a top surface of the vaginal manipulator probe through to a bottom surface of the vaginal manipulator probe.

12. The apparatus of claim 1, wherein an aperture is positioned approximately midway along a length of the arcuate end portion of the vaginal manipulator probe.

13. The apparatus of claim 1, wherein the vaginal manipulator probe incorporates a light source.

14. The apparatus of claim 1, wherein the disk is movable along a portion of a length of the vaginal manipulator probe having a notch track.

15. The apparatus of claim 1, wherein the disk includes a sleeve portion that circumscribes the vaginal manipulator probe.

16. The apparatus of claim 1, wherein the disk includes a spring loaded latch that is tensionally biased against a notch track of the vaginal manipulator probe.

17. The apparatus of claim 1, wherein the disk includes a latch having an adjustable tension lever that locks the latch in position against a notch track of the vaginal manipulator probe.

18. The apparatus of claim 1, wherein the disk includes a lateral surface that circumscribes the vaginal manipulator probe, the lateral surface being operable to rest against an outside surface of a vulva when the vaginal manipulator probe is inserted within the vagina.

19. An apparatus comprising:
    an elongated handle portion having a first end and a second end, the handle portion including a grip and an articulating joint;
    a vaginal manipulator probe that is at least partly insertable into a vagina, the vaginal manipulator probe extending from the elongated handle portion at the articulating joint and including an arcuate end portion that is curved away from a longitudinal axis of the vaginal manipulator probe to a bullous tip, the arcuate end portion including a channel that has a diameter that accommodates a cervix therewithin, the bullous tip defined by distention that increases a cross-sectional height between a bottom surface and a top surface of the vaginal manipulator probe; and
    a disk that is movable along at least a portion of a length of the vaginal manipulator probe, the disk including a locking mechanism to releasably secure the disk in position to limit vaginal insertion depth of the vaginal manipulator probe.

20. An apparatus comprising:
    a handle portion;
    a vaginal manipulator probe that is at least partly insertable into a vagina, the vaginal manipulator probe extending from the handle portion and including an arcuate end portion that is curved away from a longitudinal axis of the vaginal manipulator probe to a bullous tip, the arcuate end portion including a channel that has a diameter that accommodates a cervix therewithin, the bullous tip defined by distention that increases a cross-sectional height between a bottom surface and a top surface of the vaginal manipulator probe;
one or more LED lights disposed on the vaginal manipulator probe for illuminating vaginal tissue;
at least one battery receptacle within the handle portion;
at least one button or switch operable to control operation of the one or more LED lights; and
a disk that is movable along at least a portion of a length of the vaginal manipulator probe, the disk including a locking mechanism to releasably secure the disk in position to limit vaginal insertion depth of the vaginal manipulator probe.

* * * * *